(12) United States Patent
Gaur et al.

(10) Patent No.: US 8,106,028 B2
(45) Date of Patent: Jan. 31, 2012

(54) MICRORNA-21 ANTAGONISTS AND ITS TARGET PDCD4 FOR USE IN THE TREATMENT OF A GLIOMA

(75) Inventors: Arti Gaur, Hanover, NH (US); Mark A. Israel, Hanover, NH (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 12/948,856

(22) Filed: Nov. 18, 2010

(65) Prior Publication Data

US 2011/0118336 A1 May 19, 2011

Related U.S. Application Data

(60) Provisional application No. 61/262,184, filed on Nov. 18, 2009.

(51) Int. Cl.
*A61K 48/00* (2006.01)
*C12Q 1/70* (2006.01)
*C07H 21/04* (2006.01)
*C07H 21/02* (2006.01)

(52) U.S. Cl. ............. 514/44; 435/6; 536/23.1; 536/24.5

(58) Field of Classification Search ........................ None
See application file for complete search history.

(56) References Cited

OTHER PUBLICATIONS

Scherer et al. (Nat. Biotechnol., 2003, 21(12), pp. 1457-1465).*
Mahato et al. (Expert Opinion on Drug Delivery, Jan. 2005, vol. 2, No. 1, pp. 3-28).*
Chan et al. "MicroRNA-21 Is an Antiapoptotic Factor in Human Glioblastoma Cells" Cancer Research 2005 65(14): 6029-6033.
Chen et al. "MicroRNA-21 Down-regulates the Expression of Tumor Suppressor PDCD4 in Human Glioblastoma Cell T98G" Cancer Letters 2008 272(2):197-205.
Corsten et al. "MicroRNA-21 Knockdown Disrupts Glioma Growth In vivo and Displays Synergistic Cytotoxicity with Neural Precursor Cell-Delivered S-TRAIL in Human Gliomas" Cancer Research 2007 67(19):8994-9000.
Gabriely et al. "MicroRNA 21 Promotes Glioma Invasion by Targeting Matrix Metalloproteinase Regulators" Molecular and Cellular Biology 2008 28(17):5369-5380.
Gao et al. "Frequent Loss of PDCD4 Expression in Human Glioma: Possible Role in the Tumorigenesis of Glioma" Oncology Reports 2007 17(1):123-128.
Gaur et al. "Characterization of MicroRNA Expression Levels and Their Biological Correlates in Human Cancer Cell Lines" Cancer Research 2007 67(6):2456-2468.
Krichevsky, A. M. and Gabriely, G. "miR-21: A Small Multi-faceted RNA" Journal of Cellular and Molecular Medicine 2009 13(1):39-53.
Lankat-Buttgereit, B. and Göke, R. "The Tumour Suppressor Pdcd4: Recent Advances in the Elucidation of Function and Regulation" Biology of the Cell 2009 101(6):309-317.
Lu et al. "MicroRNA-21 Promotes Cell Transformation by Targeting the Programmed Cell Death 4 Gene" Oncogene 2008 27(31):4373-4379.
Papagiannakopoulos et al. "MicroRNA-21 Targets a Network of Key Tumor-Suppressive Pathways in Glioblastoma Cells" Cancer Research 2008 68(19):8164-8172.
Selcuklu et al. "*miR-21* as a Key Regulator of Oncogenic Processes" Biochemical Society Transactions 2009 37(4):918-925.
Zhu et al. "MicroRNA-21 Targets Tumor Suppressor Genes in Invasion and Metastasis" Cell Research 2008 18(3):350-359.

* cited by examiner

*Primary Examiner* — Amy Bowman
(74) *Attorney, Agent, or Firm* — Licata & Tyrrell P.C.

(57) ABSTRACT

The present invention embraces microRNA-21 antagonists and activators of Programmed Cell Death 4 for use in decreasing glial tumor cell proliferation and treating glioma.

2 Claims, 1 Drawing Sheet

SEQUENCE LISTING

```
<160> NUMBER OF SEQ ID NOS: 2

<210> SEQ ID NO 1
<211> LENGTH: 72
<212> TYPE: RNA
<213> ORGANISM: Homo sapiens

<400> SEQUENCE: 1
ugucggguag cuuaucagac ugauguugac uguugaaucu cauggcaaca ccagucgaug      60
ggcugucuga ca                                                         72

<210> SEQ ID NO 2
<211> LENGTH: 22
<212> TYPE: RNA
<213> ORGANISM: Homo sapiens

<400> SEQUENCE: 2
uagcuuauca gacugauguu ga                                              22
```

MICRORNA-21 ANTAGONISTS AND ITS TARGET PDCD4 FOR USE IN THE TREATMENT OF A GLIOMA

INTRODUCTION

This application claims benefit of priority to U.S. Provisional Application Ser. No. 61/262,184, filed Nov. 18, 2009, the content of which is incorporated herein by reference in its entirety.

BACKGROUND OF THE INVENTION

MicroRNAs or miRNAs are small noncoding RNAs which function by regulating target gene expression post-transcriptionally. The breadth of genetic regulatory effects potentially mediated by microRNAs and their central role in diverse cellular and developmental processes (Ambrose (2004) *Nature* 431 (7006):350-5; Bartel & Chen (2004) *Nat. Rev. Genet.* 5 (5):396-400; Miska (2005) *Curr. Opin. Genet. Dev.* 15 (5):563-8; Sevignani, et al. (2006) *Mamm. Genome* 17 (3):189-202) has led to the suggestion that aberrant expression of microRNA genes could contribute to human disease, including cancer (McManus (2003) *Semin. Cancer Biol.* 13 (4):253-8; Caldas & Brenton (2005) *Nat. Med.* 11 (7):712-4; Lu, et al. (2005) *Nature* 435 (7043):834-8; Croce & Calin (2005) *Cell* 122 (1):6-7). A substantial number of microRNA genes are located in genomic regions that are frequently amplified, deleted, or rearranged in cancer, providing further evidence of a role for microRNAs in cancer pathogenesis (Calin, et al. (2002) *Proc. Natl. Acad. Sci. USA* 99 (24): 15524-9; Nairz, et al. (2006) *Dev. Biol.* 291 (2):314-24). Deregulated microRNA expression has been documented in diverse cancers including lymphoma (Tagawa & Seto (2005) *Leukemia* 19 (11):2013-6; He, et al. (2005) *Nature* 435 (7043):828-33; Costinean, et al. (2006) *Proc. Natl. Acad. Sci. USA* 103 (18):7024-9; Kluiver, et al. (2006) *Genes Chromosomes Cancer* 45 (2):147-53 11-14), colorectal cancer (Michael, et al. (2003) *Mol. Cancer. Res.* 1 (12):882-91), lung cancer (Hayashita, et al. (2005) *Cancer Res.* 65 (21):9628-32), breast cancer (Iorio, et al. (2005) *Cancer Res.* 65 (16): 7065-70), and glioblastoma (Ciafre, et al. (2005) *Biochem. Biophys. Res. Commun.* 334 (4):1351-8; Chan, et al. (2005) *Cancer Res.* 65 (14):6029-33). Specific microRNAs have been shown to target genes critical for the development of cancer such as E2F (O'Donnell, et al. (2005) *Nature* 435 (7043):839-43) and RAS (Johnson, et al. (2005) *Cell* 120 (5):635-47). In addition, Asangani, et al. ((2008) *Oncogene* 27:2128-2136) teach that microRNA-21 (miR-21) is involved in invasion, intravasation and metastasis in colorectal cancer and post-transcriptionally down-regulates tumor suppressor Pdcd4. Hence, microRNAs and the genes they regulate can potentially provide etiologic insights as well as serve as both diagnostic markers and therapeutic targets for many different tumor types.

Gliomas are tumors that occur in the central nervous system and demonstrate invasive growth. Glioblastomas in particular are the most resistant to treatment, and have an extremely poor five-year survival rate of about 8%. Although definitive efficacy of chemotherapy has only been confirmed for alkylating agents and temozolomide, their efficacy is limited to concomitant use with radiotherapy. On the other hand, post-surgical radiotherapy has been recognized to demonstrate life-prolonging effects. Knowledge of molecular biomarkers that are associated with genetic regulatory mechanisms contributing to malignancy is essential for elucidating the mechanisms underlying malignant transformation, for understanding pathologic attributes of Glioblastoma Multiforme (GBM), and ultimately for designing effective strategies for GBM treatment. MicroRNA-21 has been identified as a molecular biomarker of GBM (Gazer, et al. (2007) *Cancer Res.* 67:2456-68) and is correlated with glioma grade (Selcuklu, et al. (2009) *Biochem. Soc. Trans.* 37 (Pt 4):918-925; Krichevsky & Gabriely (2009) *J. Cell Mol. Med.* 13 (1):39-53; Gabriely, et al. (2008) *Mol. Cell. Biol.* 28 (17):5369-5380; Chan, et al. (2005) supra; Corsten, et al. (2007) *Cancer Res.* 67 (19):8994-9000; Papagiannakopoulos, et al. (2008) *Cancer Res.* 68 (19):8164-8172). Low levels of mir-21 are expressed in Grade II and Grade III gliomas, while significantly higher levels are observed in GBM (Gabriely, et al. (2008) supra; Papagiannakopoulos, et al. (2008) supra). Chan, et al. ((2005) supra) also teach that levels of miR-21 are markedly elevated in human glioblastoma tumor tissues, early-passage glioblastoma cultures, and in six established glioblastoma cell lines, wherein knockdown of miR-21 in cultured glioblastoma cells triggers activation of caspases and leads to increased apoptotic cell death. Moreover, Papagiannakopoulos, et al. ((2008) supra) and Gabriely, et al. ((2008) supra) teach that down-regulation of miR-21 in glioblastoma cells causes repression of growth, increased apoptosis, and cell cycle arrest.

Pdcd4 (Programmed Cell Death 4), a known tumor suppressor gene, has been identified as a functional target of mir-21 (Lu, et al. (2008) *Oncogene* 27 (31):4373-4379; Zhu, et al. (2008) *Cell Res.* 18 (3):350-359) and has been shown to regulated by mir-21 in GBM (Chen, et al. (2008) *Cancer Lett.* 272 (2):197-205). However, the effect of mir-21 regulation of Pdcd4 on specific biological activities of pathologic potential such as apoptosis, proliferation, anchorage-independent growth, or more significantly in vivo growth of GBM xenografts has not been previously examined.

SUMMARY OF THE INVENTION

The present invention features methods for decreasing glial tumor cell proliferation by contacting a glial tumor cell with an effective amount of a Pdcd4 activator, so that the proliferation of the glial tumor cell is decreased as compared to a control. According to some embodiments, the glial tumor cell is an astrocytoma tumor cell, ependymal tumor cell, glioblastoma multiforme tumor cell, or primitive neuroectodermal tumor cell.

The present invention also embraces a method for treating glioma by administering to a subject in need thereof an effective amount of a Pdcd4 activator, and optionally a microRNA-21 antagonist, so that the subject's glioma is treated. In some embodiments, the glioma is an astrocytoma, ependymal tumor, primitive neuroectodermal or glioblastoma multiforme, wherein the glioblastoma multiforme is located in the brain or spinal cord of the subject, with particular embodiments embracing treatment of human subjects.

DETAILED DESCRIPTION OF THE INVENTION

Figure 1A:
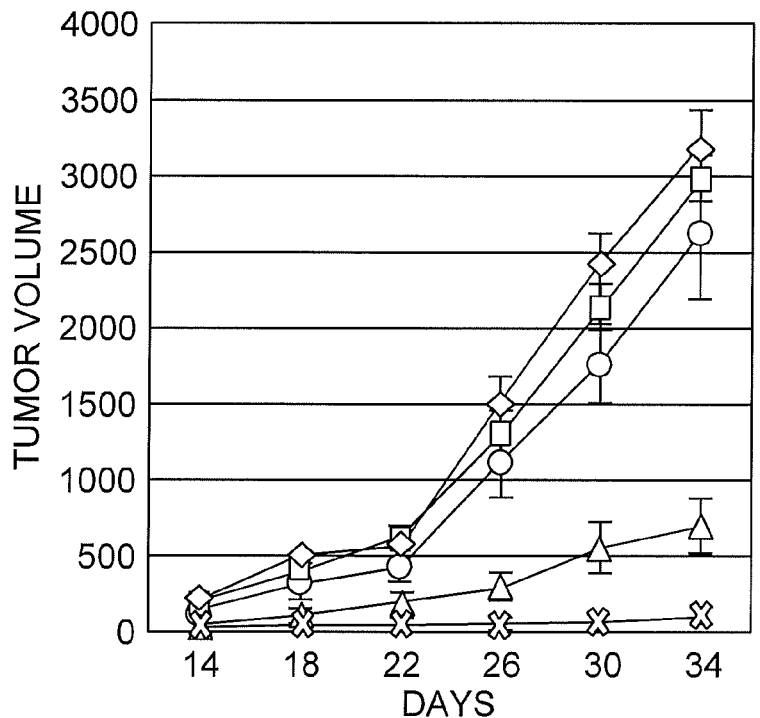
FIG. 1 shows that down-regulation of mir-21 or over-expression of Pdcd4 results in reduction of U251 (FIG. 1A) and U87 (FIG. 1B) GBM xenograft growth that is reversed by siRNA to Pdcd4. Tumor volume of xenografts that developed from $U251^{GFP}$ or $U87^{GFP}$ cells (diamond), $U251^{GFP}$ or $U87^{GFP}$ cells treated with non-specific negative/toxicity anti-mir (NS) control (30 µM; square) or anti-mir-21 (30 µM; triangle); $U251^{GFP+Pdcd4}$ and $U87^{GFP+Pdcd4}$ cells (cross); or), $U251^{GFP}$ or $U87^{GFP}$ cells treated with anti-mir-21 (30 µM) and siRNA to Pdcd4 (circle) were measured. Measurements were taken every 4 days from day 10 to day 34 post-injection. Data are averages of five independent xenograft experiments (total n=24 animals per condition)±SEM.

It has now been shown that oncogenic mir-21 is involved in regulating the pathology of glioblastoma multiforme. The data herein indicate that down regulation of mir-21 in GBM-derived cell lines results in increased expression levels of its target, Programmed Cell Death 4 (Pdcd4). Additionally, the data indicate that either down-regulation of mir-21 or overexpression of Pdcd4 in human GBM lines leads to decreased proliferation, increased apoptosis, and decreased colony formation in soft agar. Furthermore, the decreased colony formation in soft agar and increased apoptosis observed as a result of mir-21 down-regulation in GBM lines is significantly inhibited by expression of siRNAs complementary to Pdcd4 mRNA. Moreover, using a xenograft model in immune-deficient nude mice, it was shown that human GBM-derived cell lines, wherein mir-21 levels were down-regulated or Pdcd4 was over expressed, results in decreased tumor formation and tumor growth.

Accordingly, having demonstrated that expression levels of mir-21 and its target Pdcd4 are associated with pathologic characteristics of GBM in vivo, the present invention embraces the use of miR-21 antagonists and Pdcd4 activators to decrease glial tumor cell proliferation and in the treatment of glioma. In accordance with methods for decreasing glial tumor cell proliferation, a glial tumor cell is contacted with a Pdcd4 activator and optionally an agent that inhibits the expression or activity of a product of the microRNA-21 gene (i.e., a mir-21 antagonist) so that tumor cell growth is decreased or inhibited as compared to a control cell, e.g., a tumor cell not contacted with said antagonist or activator. For the purposes of the present invention, a glial tumor cell is intended to mean a tumor cell of the central nervous system, including astrocytomas, ependymal tumors, glioblastoma multiforme, and primitive neuroectodermal tumors. Inhibition of glial tumor cell proliferation can be determined by routine methods (e.g., optical density, colony counts or cell counts), wherein the antagonists or activators of the invention provide at least a 20%, 30%, 40%, 50%, 60%, 70%, 80%, 90%, 95%, 98%, or 99% decrease in the number of glial tumor cells when compared to control cells. In some embodiments, the glial tumor cell is isolated and contacted in vitro. In other embodiments, the tumor cell is contacted in vivo.

Inhibition of glial tumor cell proliferation finds application in the decreasing the size of glial tumors and in the treatment of glioma. In this respect, the present invention also embraces a method for treating glioma in a subject. This method involves administering an effective amount of a Pdcd4 activator and optionally a mir-21 antagonist to a subject in need thereof to treat the glioma.

As is conventional in the art, glioma refers to a cancer of the central nervous system that begins in glial cells (i.e., cells that surround and support nerve cells and includes oligodendrocytes, astrocytes, microglia, and ependymal cells). Gliomas are particularly serious in terms of both incidence and malignancy, and are classified into seven or more types such as glioblastoma and anaplastic astrocytoma according to their detailed pathological tissue type. Disease stage (tumor size, presence of distal metastasis) and histological malignancy are used when determining the degree of malignancy of primary brain tumors. Histological malignancy is classified into four levels, i.e., G1 to G4 according to the Guidelines for the Treatment of Brain Tumors ((2002) Kanehara & Co., Ltd.), and these correspond to WHO1 to WHO4, respectively. The larger the number, the higher the degree of malignancy. For example, the malignancy of glioblastoma is G4 (WHO4), while the malignancy of anaplastic astrocytoma is G3 (WHO3), and both G3 and G4 are classified as malignant. Thus, according to some embodiments, the methods of this invention target malignant gliomas. In other embodiments, the invention targets glioblastoma multiforme. In further embodiments, the present invention is extended to include the treatment of other gliomas including, but not limited to, anaplastic astrocytoma, giant cell glioblastoma, gliosarcoma, anaplastic oligodendroglioma, anaplastic ependymoma, choroid plexus carcinoma, anaplastic ganglioglioma, pineoblastoma, medulloepithelioma, ependymoblastoma, medulloblastoma, supratentorial primitive neuroectodermal tumor, and atypical teratoid/rhabdoid tumor.

Subjects benefiting from treatment according to the invention include subjects with a glioma, or subjects suspected of having a glioma, as evidenced by the presence of headaches, nausea and vomiting, seizures, loss of vision, pain, weakness, numbness in the extremities, and/or cranial nerve disorders as a result of increased intracranial pressure. In particular embodiments, the glioma being treated is glioblastoma multiforme. In accordance with this embodiment, the glioblastoma multiforme can be in the brain or spinal cord.

As used herein, treatment of cancer encompasses either reducing the growth of a tumor in the subject, reducing the clinical symptoms associated with tumor growth in the subject, and/or increasing survival time as compared to a subject not receiving treatment. For the purposes of the present invention, "treatment" refers to both therapeutic treatment and prophylactic or preventative measures. As such, those in need of treatment include those already with the disorder as well as those prone to have the disorder (e.g., by genetic predisposition or exposure to carcinogenic agents). Subjects benefiting from treatment in accordance with the present invention include mammals, such as humans, domestic and farm animals, and zoo, sports, or pet animals, e.g., dogs, horses, cats, cows, etc. Preferably, the mammal herein is human. Effective treatment can determined by measuring the level of expression or activity Pdcd4 and optionally the expression or activity of a product of the microRNA-21 gene.

In human, the mir-21 gene has a chromosomal position of 17q23.1 and is transcribed as a 3389 by pri-miRNA (NCBI cDNA clone BC053563). The precursor of mir-21 is 72 bases long (pre-mir-21, 5'-UGU CGG GUA GCU UAU CAG ACU GAU GUU GAC UGU UGA AUC UCA UGG CAA CAC CAG UCG AUG GGC UGU CUG ACA-3'; SEQ ID NO:1), which upon cleavage by Dicer, is further processed to a 22-bp RNA (mature mir-21, 5'-UAG CUU AUC AGA CUG AUG UUG A-3'; SEQ ID NO:2). Agents that antagonize mir-21 activity or expression include antisense, ribozyme, inhibitory RNA, or small organic molecule known in the art or identified in screening assays for binding to and inhibiting the activity or expression of mir-21. In one embodiment, the antagonist targets sequences present in the mature mir-21 molecule. In another embodiment, the antagonist is specific for the pre-mir-21 molecule and does not bind to sequences in common with the mature mir-21 molecule. In another embodiment, the antagonist is specific for the mir-21 pri-miRNA and does not bind to sequences in common with the pre-mir-21 or mature mir-21 molecules. By way of illustration, an antisense 2'-O-methyl oligonucleotide molecule complementary to the longest form of the mir-21 can be designed to specifically inactivate mir-21 activity in human cells (Meister, et al. (2004) *RNA* 10 (3) 544-550; Hutvágner, et al. (2004) *PLoS Biol.* 2 (4): e98). Alternatively, an ANTI-MIR™ miRNA Inhibitor (Ambion) for mir-21 (product ID AM12979) can be commercially obtained. Use of an mir-21 antagonistic compound will desirably reduce the expression or the activity of the microRNA by 10%, 20%, 30%, 40%, 50%, 60%, 70%, 80%, 90% or 100%. Such decreases can be monitored by detecting the level of mir-21, or target mRNA (i.e., mRNA encoding Pdcd4) or detecting the level of the protein product translated from the target mRNA (i.e., Pdcd4) and comparing said levels with those in control cells not contacted with the mir-21 antagonist. In one embodiment, the microRNA-21 antagonist specifically antagonizes mir-21, i.e., it fails to antagonize any other transcript in the cell.

As indicated, the present invention also embraces the use of agents that increase the expression or activity of Pdcd4, referred to herein as Pdcd4 activators, to decrease proliferation of glial tumor cells, reverse the transformed status of glioma tumor cells and prevent and/or treat glioma. Activators of the invention include nucleic acid molecules, proteins or small molecules that increase the expression or activity of Pdcd4. For example, RAR pan-agonists and Am580 have been shown to stimulate the expression of PDCD4 in breast cancer cells (Afonja, et al. (2004) *Oncogene* 23 (49):8135-45). In addition, nucleic acids encoding Pdcd4 can be used to exogenously increase expression. Nucleic acids encoding Pdcd4 are well-known to the skilled artisan and available under GENBANK Accession Nos. NM_014456 and NM_145341. Said nucleic acids can be provided to a cell or subject as naked DNA, in expression vectors (e.g., adenoviral, adeno-associated viral, or lentiviral vectors), or in carriers such as liposomes routinely used in the art to facilitate the delivery and expression of nucleic acids in vivo. Alternatively, Pdcd4 can be provided to a cell or subject in the form of a purified protein prepared and isolated by conventional recombinant protein expression technologies. The amino acid sequence of human Pdcd4 and its homologs is well-known and available, e.g., under GENBANK Accession Nos. NP_055271 and NP_663314. Desirably, an activator of the invention increases the expression or activity of Pdcd4 by at least 10%, 20%, 30%, 40%, 50%, 60%, 70%, 80%, 90% or 100% as compared to cells or subjects not contacted with the activator.

Effective amounts of antagonists and activators disclosed herein will depend upon the mode of administration, frequency of administration, nature of the treatment, age and condition of the individual to be treated, and the type of pharmaceutical composition used to deliver the antagonist or activator into a living system. While individual doses can vary, optimal ranges of effective amounts can be determined by one of ordinary skill in the art. For example, the safe and effective dosages identified in clinical trials can be considered when selecting dosages for treatments according to the present invention.

Antagonists and activators used in the methods of the present invention can be administered alone or as a pharmaceutical composition, which includes the compound(s) and a pharmaceutically-acceptable carrier. A pharmaceutical composition can include suitable excipients, or stabilizers, and can be in solid or liquid form such as, tablets, capsules, powders, solutions, suspensions, or emulsions. Typically, the composition will contain from about 0.01 to 99 percent, preferably from about 5 to 95 percent of active compound(s), together with the carrier.

Antagonists and activators of the invention, when combined with pharmaceutically or physiologically acceptable carriers, excipients, or stabilizers, whether in solid or liquid form such as, tablets, capsules, powders, solutions, suspensions, or emulsions, can be administered orally, parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes, such as, that of the nose, throat, and/or bronchial tubes (i.e., inhalation).

For most therapeutic purposes, an antagonist or activator of the invention can be administered orally as a solid or as a solution or suspension in liquid form, via injection as a solution or suspension in liquid form, or via inhalation of a nebulized solution or suspension. The solid unit dosage forms can be of the conventional type. The solid form can be a capsule, such as an ordinary gelatin type containing the compound(s) of the present invention and a carrier, for example, lubricants and inert fillers such as, lactose, sucrose, or cornstarch. In another embodiment, compounds are tableted with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

For injectable dosages, solutions or suspensions of an antagonist or activator of the invention can be prepared in a physiologically acceptable diluent with a pharmaceutical carrier. Such carriers include sterile liquids, such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose, and related sugar solution, and glycols, such as propylene glycol or polyethylene glycol, are preferred liquid carriers, particularly for injectable solutions.

For use as aerosols, an antagonist or activator of the invention in solution or suspension may be packaged in a pressurized aerosol container together with suitable propellants, for example, hydrocarbon propellants like propane, butane, or isobutane with conventional adjuvants. The agent of the present invention also can be administered in a non-pressurized form such as in a nebulizer or atomizer.

For transdermal routes, an antagonist or activator of the invention is present in a carrier which forms a composition in the form of a cream, lotion, solution, and/or emulsion. The composition can be included in a transdermal patch of the matrix or reservoir type as are conventional in the art for this purpose.

It is also contemplated that administration of an antagonist or activator of the invention can be carried out in combination with other suitable therapeutic treatments that are useful for treating glial tumors. For example, an antagonist or activator of the invention can be combined with surgery, radiation therapy, and/or chemotherapy in the treatment of a glioma. Examples of chemotherapeutic agents which can be used in a combination treatment include, but are not limited to, temozolomide (TEMODAR; Schering Plough), irinotecan (CAMPTOSAR; Rhone Puolenc Rorer), carboplatin (PARAPLATIN; Bristol-Myers Squibb), oxaliplatin (ELOXATIN; Sanofi-Aventis), nitrosoureas, lomustine (CEENU; Bristol-Myers Squibb), vincristine (ONCOVIN; Gensia Sicor), vinblastine (VALBAN; Gensia Sicor), procarbazine (MATULANE; Sigma-tau), EGF receptor blockers such as cetuximab (ERBITUX; Imclone Systems), pertuzumab (OMNITARG, Genentech), erlotinib (TARCEVA, OSI), gefitinib (IRESSA, AstraZeneca) and imatinib mesylate (GLEEVEC, Novartis), multi-targeted tyrosine kinase inhibitors such as sorafenib (NEXAVAR, Bayer) or sunitinib malate (SUTENT, Pfizer). Additional therapeutics useful in the method of the invention include sirolimus (RAPAMUNE; Wyeth), RAD001 (Novartis), Sutan, Divalproes (DEPAKOTE; Abbott), and p13K and AKT inhibitors.

The invention is described in greater detail by the following non-limiting examples.

Example 1

Materials and Methods

Tissue Samples. GBM specimens and normal brain tissue were from the Neurosurgery Tissue Bank at the University of California San Francisco. All samples were obtained with informed consent.

Cell Lines and Culture Conditions. GBM cell lines SNB19, U251, U87 and SF767 were cultured in Dulbecco's Modified Eagle's Medium/10% fetal bovine serum (FBS)/1% penicillin (10,000 units/mL)/streptomycin (10,000 µg/mL). All cells were grown in a humidified incubator in 5% $CO_2$ at 37° C.

Derivation of Stable, Polyclonal Cultures and Monoclonal Cell Lines Expressing Pdcd4. To derive stable Pdcd4 expressing polyclonal cultures, U251 and U87 cell lines were transfected with pcDNA-Pdcd4 and cells were selected for three weeks with 500 µg/ml of Geneticin. Subsequently, cultures were expanded and maintained in 200 µg/ml of Geneticin. To derive stable GFP and Pdcd4 expressing polyclonal cultures, U87 and U251 cell lines were transfected first with pEGFP (CLONTECH, Mountain View, Calif.) and cells were selected for three weeks with hygromycin (100 µg/ml hygromycin). Cells were then transfected with pcDNA-Pdcd4 and selected as described above. Monoclonal $U25^{Pdcd4}$ or $U87^{Pdcd4}$ as well as $U251^{GFP+Pdcd4}$ or $U87^{GFP+Pdcd4}$ cultures were derived from single cells seeded in 96-well plates.

Transient Expression of Anti-mirs and siRNAs. ANTI-MIR™-21 miRNA Inhibitor, ANTI-MIR™ miRNA Inhibitors-Negative/toxicity Control and FAM™ dye-labeled ANTI-MIR™ were purchased from Applied Biosystems/Ambion (Austin, Tex.). Pre-designed siRNA constructs complementary to Pdcd4 were obtained from Ambion (Silencer Select, siRNA ID s26048, Applied Biosystems/Ambion, Austin, Tex.). Transient transfections were carried out using SIPORT™ NEOFX™ Transfection Agent (Applied Biosystems/Ambion, Austin, Tex.) per the manufacturer's instructions. During the transfection, cells were cultured in reduced serum OPTIMEM medium (Invitrogen, Carlsbad, Calif.).

Real-Time Quantification of MicroRNAs using Stem-Loop Real-Time PCR. The expression profiles of 241 microRNAs were measured according to known methods (Gaur, et al. (2007) supra). The method employed stem-loop primers for reverse transcription followed by real-time PCR (TAQMAN MicroRNA Assays; Applied Biosystems, Foster City, Calif.). Expression of mature miRNAs was determined by the TAQMAN miRNA assay (Applied Biosystems, Foster City, Calif.). The TAQMAN primer-probe for quantification of miR-21 (for the target sequence 5'-UAG CUU AUC AGA CUG AUG UUG A-3'; SEQ ID NO:2) was from Applied Biosystems (Foster City, Calif.). RNA input was normalized using four endogenous controls: 18S rRNA, β2M, glyceraldehyde-3-phosphate dehydrogenase, and β-actin.

Western Blot Analysis to Detect Pdcd4 Protein. To obtain whole-cell lysates, cells were sonicated and then lysed on ice for 30 minutes in lysis buffer (50 mmol/L Tris-HCl, 150 mmol/L NaCl, 5 mmol/L EDTA, 0.5% NP40, 1 mmol/L phenylmethylsulfonyl fluoride (PMSF), and complete protease inhibitor cocktail mix (Roche, Indianapolis, Ind.)). Protein concentration was determined by BCA (Pierce, Rockford, Ill.). For western blot analysis, 40 µg of protein were separated on a 10% SDS-PAGE and transferred to a nitrocellulose membrane. Pdcd4 was detected using a affinity-purified rabbit anti-Pdcd4 antibody (Rockland, Gilbertsville, Pa.) at a 1:5000 dilution as the primary antibody followed by a alkaline phosphatase-linked goat anti-rabbit secondary antibody (Abcam, Cambridge, Mass.) used at 1:50000 dilution. To detect TATA binding protein (TBP) as a loading control, a mouse monoclonal antibody to TBP (Abcam, Cambridge, Mass.) was used at 1:3000 as the primary antibody followed by a alkaline phosphatase-linked rabbit anti-mouse (Abcam, Cambridge, Mass.) secondary antibody used at 1:5000. Following incubation of the membranes with the specific antibodies, proteins were visualized by chemiluminescence (ECL, Amersham, Freiburg, Germany). To detect Pdcd4 in tumors, tumor tissues were first homogenized using a sonicator, and proteins were extracted and processed as described above.

Northern Analysis to Detect miRNAs. Total RNA was extracted from GBM specimens, normal brain tissue or from GBM-derived cell lines with TRIZOL Reagent following the vendor's recommendations. Twenty µg of total RNA was separated on a 10% urea-polyacrylamide gel and transferred to a GENESCREEN Plus (PerkinElmer, Waltham, Mass.). Radioactive-labeled STARFIRE (Integrated DNA Technologies, Coralville, Iowa) oligonucleotide probes were used for miRNA detection. Membranes were stripped by boiling in 0.1% SDS and re-hybridized to U6 probe for to determine loading controls.

Proliferation Assays. U251 or U87 cells (50,000 cells) that were untreated or transfected with a non-specific negative/toxicity anti-mir (NS) control (30 µM) or anti-mir-21 (3, 10, and 30 µM) were seeded onto a 10-cm tissue culture dish at day 0. Growth curves were determined by counting cells every 24 hours for five days with a hemacytometer.

Anchorage-Independent Growth Assay in Soft Agar. Anchorage-independent growth assays were performed by seeding $1 \times 10^5$ cells in 0.4% Noble agar on an 0.8% agar base layer, both of which contained Dulbecco's Modified Eagle's Medium/10% fetal bovine serum (FBS)/1% penicillin (10,000 units/mL)/streptomycin (10,000 µg/mL). Colonies were counted (>0.1-mm) 2 weeks after seeding, and the data from triplicate determinations were expressed as mean±SEM.

Apoptosis Assays. Cells were cultured on four-well LAB-TEK II Chamber Slides (Nunc/Thermo Fisher Scientific, Rochester, N.Y.) and anti-mir and negative/toxicity (NS) control transfections were carried out in the chambers. Forty-eight hours post-transfection, cells were fixed in 4% paraformaldehyde and the chambers were removed. For labeling nuclei of apoptotic cells, terminal deoxynucleotidyl transferase-mediated nick-end labeling (TUNEL) was done using the DEADEND fluorometric TUNEL system (Promega, Madison, Wis.) according to the manufacturer's protocol. Cell nuclei were also stained with Hoechst dye. The number of TUNEL-positive cells was divided by the number of Hoechst-stained cells to yield the percent apoptotic nuclei. Four 40× objective fields containing 200 cells each were counted per chamber, with three chambers analyzed per condition.

Xenograft Growth in Athymic Nude Mice. Female, 4-6 week-old Nude-Foxn1$^{nu}$ mice (Harlan, Indianapolis, Ind.) were injected with PBS-washed cells ($5 \times 10^6$ cells) subcutaneously in the flank. Tumor size was measured in three dimensions with calipers, and volume was calculated assuming the shape as ellipsoid. All animal studies were conducted using procedures outlined by the Association for Assessment and Accreditation of Laboratory Animal Care (AAALAC) and the Institutional Animal Care and Use Committee (IACUC). The IVIS 200 Xenogen Imaging System (Caliper Life Sciences, Hopkinton, Mass.) was used to detect tumors in vivo.

Statistical analysis. Data are represented as the mean±standard deviation (SD) or ±standard error of the mean (SEM) as indicated. Differences were analyzed by using an unpaired two-tailed Student t test and p<0.05 was considered statistically significant. All of the experiments were performed at least three times.

Example 2

Overexpression of Mir-21 in Primary GBM Tumors

Having identified mir-21 as a potentially oncogenic microRNAs that is highly up regulated in human GBM lines (Gaur, et al. (2007) supra), it was determined whether mir-21 was also up-regulated in GBM primary tumors when compared to normal brain tissue. Using northern blot analysis, it was confirmed that mir-21 was over-expressed in GBM primary tumors as well as GBM-derived lines when compared to normal brain tissue. Comparable results were obtained using a highly sensitive technique that utilizes stem-loop primers for reverse transcription followed by real-time quantification of mir-21. In total, elevated levels of miR-21 were observed in all seven GBM-derived cell lines and in all thirteen primary GBM tumors examined. This is significant given that so far no common genetic marker has been identified for GBMs, which in general have a diverse number of proto-oncogenes and tumor suppressor genes often mutated, deleted or amplified. Considering mir-21 is the common upregulated biomarker, identifying molecular targets of miR-21 and their functions in the context of GBM initiation and progression is critical.

GBM are known to harbor diverse oncogenes and mutated tumor suppressor genes whose pattern of alteration and expression varies considerably from tumor to tumor (Holland (2001) *Nat. Rev. Genet.* 2:120-129). However, most GBM examined to date have high levels of mir-21 expression (Krichevsky & Gabriely (2009) supra; Chan, et al. (2005) supra; Gabriely, et al. (2008) supra; Corsten, et al. (2007) supra; Chen, et al. (2008) supra). Since Pdcd4 is a target of mir-21 (Lu, et al. (2008) supra) its regulation in GBM was characterized. It was contemplated that as a target transcript encoding a protein involved in tumor suppression, the expression of Pdcd4 should be decreased in GBM-derived cell lines. GBM-derived cell lines U251 and U87, in which mir-21 is highly expressed, were evaluated and it was found that Pdcd4 protein levels were undetectable. Additional evidence was sought to corroborate the association of endogenous Pdcd4 protein with endogenous miR-21 in vitro. Pdcd4 expression was assessed in GBM-derived cell lines in which mir-21 expression had been experimentally decreased using an ANTI-MIR™ miRNA inhibitor, anti-mir-21, that decreases the cellular levels of mir-21 specifically. After confirming that mir-21 levels in GBM cell lines remained down-regulated and undetectable by northern blot analysis for up to 120 hours post-transfection with anti-mir-21, U251 and U87 cells were transiently transfected with anti-mir-21 and cells were harvested at 24, 48 or 72 hours; a time window was found to be optimal for detecting the up-regulation of mir-21 target proteins. To ensure that the down regulation of mir-21 by anti-mir-21 was specific and not due to non-specific toxicity, a non-specific anti-mir (NS) was included as a negative toxicity control for each transfection. Additionally, a FAM dye-labeled, non-specific anti-mir was also used to determine transfection efficiency for each experiment. A transfection efficiency of 80-90% was routinely achieved. At each examined time point following transfection, anti-mir-21-treated and control cells were collected and divided into two identical aliquots from which total RNA and nuclear proteins were respectively isolated. Northern blot analyses demonstrated decreased levels of mir-21 in U251 and U87 cells 24, 48, and 72 hours post-transfection with anti-mir-21. Western blot analyses of nuclear proteins isolated from these same U251 and U87 cultures exhibited increased Pdcd4 protein levels 24, 48, and 72 hours after anti-mir-21 treatment. These data are consistent with the regulation of Pdcd-4 by mir-21. Additionally, the miRNA expression levels from the NCI60 glioma-derived cell lines were compared to RNA, DNA, and protein expression data for the same cell lines. This analysis indicated a significant inverse correlation (P=0.004) between miR-21 and Pdcd4 protein expression levels.

Example 3

Inhibition of Mir-21 Expression in GBM Cell Lines

Mir-21 has been shown to act as an anti-apoptotic factor in GBM-derived cell lines (Krichevsky & Gabriely (2009) supra; Chan, et al. (2005) supra) and conversely Pdcd4 has been shown to be pro-apoptotic (Lankat-Buttgereit & Göke (2009) *Biol. Cell* 101 (6):309-317). Having observed an inverse correlation between expression of mir-21 and Pdcd4 in GBM, the biological effect of mir-21 expression in GBM-derived cell lines was determined. U251 and U87 cells were transfected with varying concentrations of anti-mir-21 (3, 10, and 30 µM) and cell number was assessed every 24 hours post-transfection for five days. Down regulation of mir-21 in the anti-mir-21-treated cells was confirmed by northern blot analyses on days 1 and 5. Decreased cell numbers were observed in cultures treated with anti-mir-21 compared to cultures that were incubated in regular media or transfected with a non-specific negative toxicity control. It was also observed by TUNEL staining that U251 cells treated with anti-mir-21 exhibited enhanced apoptosis, as compared to cells cultured in either medium alone or with non-specific negative toxicity control. U87 cells treated with anti-mir-21 also demonstrated enhanced apoptosis that was detected by TUNEL staining. Although the enhanced apoptosis was easily recognizable in anti-mir-21-treated GBM cells, it was determined whether these cells exhibited decreased proliferation to better understand the remarkable difference in cell numbers in the treated cultures. Cell cycle analysis revealed that anti-mir-21 treatment of U251 and U87 cells significantly increased the number of cells in G0/G, while decreasing the fraction of cells present in S-phase (Table 1).

TABLE 1

| Cells | | | | |
|---|---|---|---|---|
| Parental | | % Cells Per Cell Cycle Phase | | |
| Cell Line | Treatment | G0/G1 | S | G2/M |
| U251 | Untreated | 58.5 ± 1.3 | 26.71 ± 0.9 | 14.74 ± 0.6 |
|  | Anti-NS control | 57.78 ± 2.1 | 27.2 ± 0.4 | 15 ± 0.7 |
|  | Anti-mir-21 | 67.2 ± 0.7 | 23.1 ± 0.2 | 9.64 ± 0.3 |
|  | U251$^{Pdcd4}$ | 69.02 ± 3.5 | 21.02 ± 0.7 | 10.03 ± 0.4 |
| U87 | Untreated | 60.1 ± 0.22 | 27.45 ± 0.2 | 12.03 ± 0.3 |
|  | Anti-NS control | 59.06 ± 1.4 | 27.19 ± 1.3 | 13.5 ± 0.8 |
|  | Anti-mir-21 | 66.4 ± 0.8 | 22.9 ± 0.8 | 10.47 ± 0.2 |
|  | U87$^{Pdcd4}$ | 70.83 ± 2.5 | 23.5 ± 1.1 | 5.66 ± 0.1 |

Pdcd4 is expressed in normal brain tissue (Chen, et al. (2005) *Nucleic Acids Res.* 33 (20):e179; Gao, et al. (2007) *Oncol Rep.* 17 (1):123-128). While Pdcd4 is not detectable in GBM tumors or GBM-derived cell lines (Gao, et al. (2007) supra), suppression of mir-21 results in increased Pdcd4 expression in these tissues. Therefore, beyond determining the biological effects of down regulating mir-21 in GBM, it was determined whether Pdcd4 was a critical target of mir-21 and mediated the specific effects of mir-21 that could contribute to GBM tumorigenesis. Accordingly, U251 and U87 cell lines were transfected with a Pdcd4 cDNA expression construct (pcDNA-Pdcd4) to generate stable GBM-derived cell cultures that over-express Pdcd4 (U251$^{Pdcd4}$ and U87$^{Pdcd4}$). Clonal isolates as well as a polyclonal culture of U251 over-expressing Pdcd-4, U251$^{Pdcd4}$, demonstrated increased spontaneous apoptosis as determined by TUNEL staining when compared to the parental cells from which they were derived. Increased apoptosis in U87 cells treated with anti-mir-21 or stably over expressing Pdcd4 (U87$^{Pdcd4}$) was also observed.

Anchorage-independent growth as assayed in soft agar is a characteristic of transformed cells that correlates closely with their tumorigenicity. U251 and U87 can grow in an anchorage-independent manner and form colonies in soft agar. Hence, to examine the role of mir-21 and its target Pdcd4 in anchorage-independent growth, the effect of inhibiting mir-21 expression on colony formation in soft agar was examined. U251 and U87 cells treated with anti-mir-21 for 72 hours and plated in soft agar displayed decreased anchorage-independent growth and formed fewer colonies (Tables 2 and 3) when compared to controls. The U251$^{Pdcd4}$ and U87$^{Pdcd4}$ polyclonal cell culture showed a decrease in colony number compared to cells that did not have elevated Pdcd-4 levels. These data are representative of U251$^{Pdcd4}$ and U87$^{Pdcd4}$ polyclonal cultures and monoclonal cell lines. In three independent experiments the number of colonies formed following exposure to anti-mir-21 decreased by approximately 65% (10 μM anti-mir-21) and 75% (30 μM anti-mir-21).

TABLE 2

| Treatment | Number of Colonies (2.5 × 10$^4$ cells/well) | Number of Colonies (5 × 10$^4$ cells/well) |
|---|---|---|
| Untreated U251 | 346 ± 47 | 663 ± 71 |
| U251 + NS Control (30 μM) | 299 ± 26 | 537 ± 39 |
| U251 + anti-mir-21 (30 μM) | 98 ± 12 | 172 ± 34 |
| U251$^{Pdcd4}$ | 11 ± 3 | 14 ± 5 |
| U251 + anti-mir-21 (30 μM) + siRNA to Pdcd4 (10 μM) | 255 ± 44 | 540 ± 68 |

Colony numbers are the averages of six determinations per condition ± SEM

TABLE 3

| Treatment | Number of Colonies (2.5 × 10$^4$ cells/well) | Number of Colonies (5 × 10$^4$ cells/well) |
|---|---|---|
| Untreated U87 | 540 ± 27 | 961 ± 54 |
| U87 + NS Control (30 μM) | 278 ± 11 | 459 ± 36 |
| U87 + anti-mir-21 (30 μM) | 114 ± 19 | 186 ± 21 |
| U87$^{Pdcd4}$ | 7 ± 0.8 | 39 ± 11 |
| U87 + anti-mir-21 (30 μM) + siRNA to Pdcd4 (10 μM) | 306 ± 46 | 499 ± 77 |

Colony numbers are the averages of six determinations per condition ± SEM

The experiments described above indicate that decreased expression of mir-21 in GBM-derived cell lines results in decreased anchorage-independent growth and decreased xenograft tumor formation. Pdcd4 has a binding site for mir-21 and the inverse correlation between mir-21/Pdcd4 levels indicates that mir-21 regulates Pdcd4. However, as mir-21 can potentially target several genes (Krichevsky & Gabriely (2009) supra), it was determined whether the biologic effects observed following inhibition of mir-21 were a consequence of Pdcd4 being targeted by mir-21. Accordingly, colony formation by U251 or U87 cells that were treated for 72 hours with either anti-mir-21 or with anti-mir-21 and siRNA to Pdcd4 was monitored. U251 or U87 cells treated for 72 hours with anti-mir-21 formed 70% and 60% fewer colonies respectively than control cells. When compared to cells that were treated with anti-mir-21 only, U251 or U87 that were treated with anti-mir-21 and siRNA to Pdcd4 produced higher number of colonies, similar to those formed by untreated U251 or U87 (Tables 2 and 3). Western blot analyses was used to monitor Pdcd4 levels in U251 or U87 cells that were untreated, treated with a non-specific negative/toxicity anti-mir control, anti-mir-21, or anti-mir-21 and siRNA to Pdcd4. U251$^{Pdcd4}$ and U87$^{Pdcd4}$ cell lines were also examined to confirm the effect of over-expressed Pdcd4 on anchorage-independent growth. The results of this analysis demonstrated a decrease in number of colonies formed in soft agar compared to cells that did not have elevated Pdcd-4 levels (Tables 2 and 3).

Example 4

Ablation of GBM Xenograft Growth

Figure 1B:
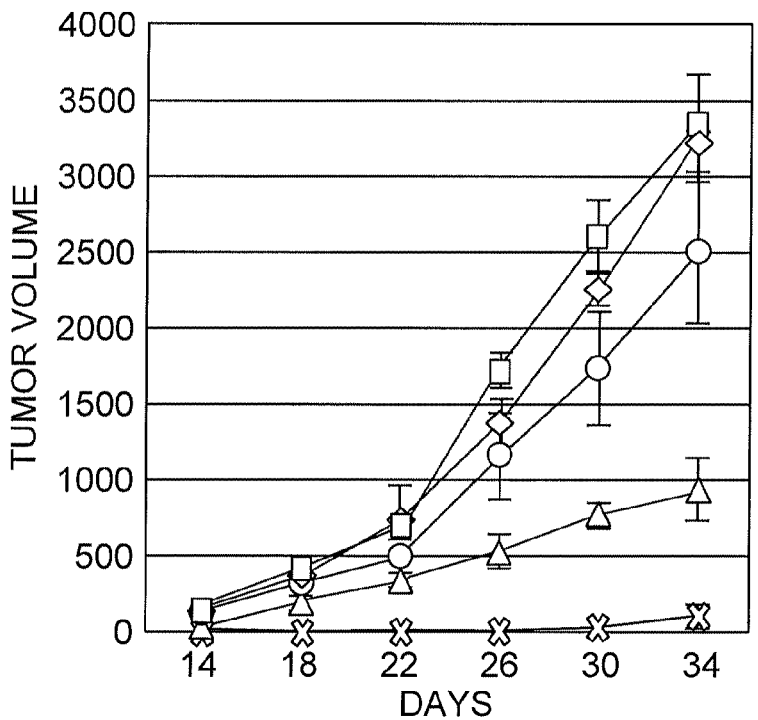

In addition to being a pro-apoptotic gene, Pdcd4 is a suppressor of malignant transformation and tumor progression and has been shown to inhibit invasion and intravasation by tumor cells (Lu, et al. (2008) supra; Young, et al. (2003) *Trends Mol. Med.* 9 (1):36-41; Allgayer (2009) *Crit. Rev. Oncol. Hematol.* 73 (3):185-191; Lankat-Buttgereit & Göke (2009) supra; Göke, et al. (2004) *Ann. NY Acad. Sci.* 1014: 220-221). Having established that GBM-derived cell lines displayed decreased proliferation and colony formation in vitro when mir-21 expression was decreased or Pdcd4 was increased, the role of mir-21 and its target Pdcd4 in GBM tumorigenesis in vivo was determined by evaluating GBM xenografts in immune-deficient mice. Polyclonal cultures of U251$^{GFP}$ and U87$^{GFP}$ cells stably expressing green fluorescent protein (GFP) were prepared. Mir-21 expression was then inhibited in these lines by treating them with anti-mir-21 (30 μM for 72 hours). U87 and U251 cell lines over-expressing GFP as well as Pdcd4 (U251$^{GFP+Pdcd4}$ and U87$^{GFP+Pdcd4}$) were also prepared. Subcutaneous injection of 5×10$^6$ cells from U251$^{GFP}$ or U87$^{GFP}$ in the flank of immunosuppressed mice gave rise to tumors that were first palpable by day 7 post-injection and developed to approximately 1.5 cm$^3$ in size by day 30. A Xenogen Imaging System was used to detect these tumors in vivo. Animals that received U251$^{GFP}$ or U87$^{GFP}$ lines were also analyzed following transfection with anti-mir-21. Suppression of mir-21 in these cell lines was confirmed by northern blot analysis. Each of these cell cultures demonstrated decreased tumor growth in vivo. Mice that received cell lines over-expressing Pdcd4, U251$^{GFP+Pdcd4}$ or U87$^{GFP+Pdcd4}$ also had tumors that were reduced in size and numbers compared to tumors arising in animals injected with the same cells bearing only GFP and not over-expressing Pdcd4. However, animals that received U251$^{GFP}$ or U87$^{GFP}$ lines following transfection with anti-mir-21 and siRNA to PDCD4, gave rise to tumors that developed to approximately 1.5 cm$^3$ in size by day 30, comparable to the control, untreated GBM-derived cell lines. Suppression of Pdcd4 in these cell lines was confirmed by western blot analysis. Tumor growth was monitored for up to 6 weeks following the inoculation of these animals with tumor cells. Tumor growth was measured every 4 days starting at day 10-post injection (FIG. 1). In all of the experiments, tumor growth was reduced by approximately 30% at day 30 (P=0.01) in mice that were injected with anti-mir-21 transfected U251$^{GFP}$ or U87$^{GFP}$ cells. Similarly, an approximately 90% (P=0.001) decrease in tumor size or complete lack of tumor growth was observed in mice that were injected with Pdcd4 over-expressing U87$^{GFP+Pdcd4}$ or U87$^{GFP+Pdcd4}$ cells. In the five independent xenograft experiments carried out examining U251$^{GFP+Pdcd4}$ or U87$^{GFP+Pdcd4}$ only 5 of 24 and 4 of 24 mice, respectively, developed tumors detectable by day 30. These tumors were, on average, 90% smaller than the tumors that arose following injection with untreated or non-specific negative/toxicity control treated U251$^{GFP}$ or U87$^{GFP}$ cells. However, the fact that some tumors, albeit much smaller than those formed in the control groups, did develop in U251$^{GFP+Pdcd4}$- or U87$^{GFP+Pdcd4}$-derived xenografts provided an opportunity to examine Pdcd4 levels in such tumors. Although the xenografts were not of sufficient size to analyze DNA, RNA, and protein, Pdcd4 protein levels were measured and it was found that Pdcd4 levels were undetectable by western blot analysis of four individual tumors that arose from animals injected with U251$^{GFP+Pdcd4}$ or U87$^{GFP+Pdcd4}$ lines. This finding indicates that these tumors were formed by cells that do not express Pdcd4.

Although an additional pathway of Pdcd4 inactivation is the increased proteasomal degradation of Pdcd4 due to its phosphorylation by Akt and p70 (S6K) (Schmid, et al. (2008) *Cancer Res.* 68 (5):1254-1260), the findings provided herein indicate that inhibition of Pdcd4 by mir-21 over-expression contributes to GBM growth. Interestingly, cells treated with anti-mir-21 and siRNA to Pdcd4 produced about 85% of the colonies compared to cells treated with anti-mir-21 only. Not to be bound by theory, this finding could indicate that mir-21 also inhibits other genes contributing to the malignant characteristics of GBM cells. For example, miR-21 has been shown to inhibit apoptosis by regulating Bcl-2 in murine breast cancer model (Wickramasinghe, et al. (2009) *Nucleic Acids Res.* 37 (8):2584-2595; Si, et al. (2007) *Oncogene* 26 (19):2799-2803) and gemcitabine-induced apoptosis by modulating PTEN and the PI-3-kinase pathway (Zhou, et al. (2010) *Lab Invest.* 90:144-155). Consistent with this is the observation that mir-21 regulates two important matrix metalloproteinase inhibitors, RECK and TIMP3, which may be of importance in vivo (Gabriely, et al. (2008) supra).

---

What is claimed is:

1. A method for decreasing glioblastoma multiforme tumor cell proliferation comprising contacting a glioblastoma multiforme tumor cell with an effective amount of a compound that increases expression of Programmed Cell Death 4, wherein said compound is selected from the group consisting of RAR panagonists, Am580 and nucleic acids encoding Pdcd4, thereby decreasing the proliferation of the glioblastoma multiforme tumor cell as compared to a control.

2. The method of claim 1, further comprising administering an effective amount of a microRNA-21 antagonist.

* * * * *